United States Patent [19]
Livesey et al.

[11] Patent Number: 5,919,614
[45] Date of Patent: *Jul. 6, 1999

[54] COMPOSITION COMPRISING THREE PLATELET LESION INHIBITORS FOR PLATELET STORAGE

[75] Inventors: Stephen A. Livesey, Conroe; Jerome Connor, The Woodlands; Laura M. Currie, Houston, all of Tex.

[73] Assignee: LifeCell Corporation, The Woodlands, Tex.

[*] Notice: This patent is subject to a terminal disclaimer.

[21] Appl. No.: 08/852,921

[22] Filed: May 8, 1997

Related U.S. Application Data

[60] Continuation-in-part of application No. 08/844,021, Apr. 18, 1997, abandoned, which is a division of application No. 08/326,036, Oct. 19, 1994, Pat. No. 5,622,867.

[51] Int. Cl.$^6$ ...................................................... A01N 1/02
[52] U.S. Cl. ............................................ 435/2; 424/93.72
[58] Field of Search .............................. 435/2; 424/93.72

[56] References Cited

U.S. PATENT DOCUMENTS

| | | | |
|---|---|---|---|
| 4,665,088 | 5/1987 | Apitz-Castro et al. | 514/420 |
| 4,764,463 | 8/1988 | Mason et al. | 424/101 |
| 4,940,581 | 7/1990 | Mason et al. | 424/532 |
| 4,983,514 | 1/1991 | Weithmann et al. | 435/29 |
| 4,994,367 | 2/1991 | Bode et al. | 435/2 |
| 5,256,559 | 10/1993 | Maraganore et al. | 435/240.2 |
| 5,622,867 | 4/1997 | Livesey et al. | 435/2 |

FOREIGN PATENT DOCUMENTS

| | | | |
|---|---|---|---|
| 0108588 | 5/1984 | European Pat. Off. | A01N 1/02 |
| 0291873 | 11/1988 | European Pat. Off. | C12Q 1/56 |
| WO90/0612 | 6/1990 | WIPO | A61K 37/02 |
| WO94/02015 | 2/1994 | WIPO | A01N 1/02 |

OTHER PUBLICATIONS

Angelini et al., "Evaluation of four different methods for platelet freezing, in–vitro and in–vivo studies", Vox Sang 62 (3): 146–151 (1992).

Contant et al., "Heparin Inactivation During Blood Storage: Its Prevention by Blood Collection in Citric Acid, Theophylline, Adenosine, Dipyridamole—CTAD Mixture", Thrombosis Research, vol. 31, No. 2, pp. 365–374, Jul. 15, 1983.

Murakami et al., "Potentiating Effect of Adenosine on Other Inhibitors of Platelet Aggregation", Thrombosis et Diathesis Haemorrhagica, vol. 27, No. 2, pp. 252–262, Apr. 30, 1972.

Bode et al., "The Use of Inhibitors of Platelet Activation or Protease Activity in Platelet Concentrates Stored for Transfusion", Blood Cells, vol. 18, No. 3, pp. 361–380, 1992.

Teng et al., "Triwaglerin: a potent platelet aggregation inducer purified from *Trimeresurus wagleri* snake venom", Biochimica et Biophysica Acta. 992 (1989) pp. 258–264.

Teng et al., "Platelet Aggregation Induced by Equinatoxin", Thrombosis Research, vol. 52, 1988) pp. 401–411.

Narayanan, "Inhibition of In Vitro Platelet Aggregation and Release and Fibrinolysis", Annals of Clinical and Laboratory Science, vol. 19, No. 4, pp. 260–265.

Valari et al., "A Simple Method for Freezing Human Platelets Using 6% Dimethylsolfoxide and Storage at —80° C.", Blood, vol. 43, No. 1 (Jan.), 1974 pp. 131–136.

Bode, et al., "Extended Storage of Platelets in an Artificial medium with the Platelet Activation Inhibitors Prostaglandin $E_1$ and Theophylline", Vox Sang 1991, pp. 105–112.

Forrester et al., "Aggregation of Platelets by *Fusobacterium necrophorum*", Journal of Clinical Microbiology, vol. 22, No. 2, Aug. 1985, pp. 245–249.

Canizares, et al., "Role of the microtubular system in platelet aggregation", Brazilian J Med Biol Res, (1994) 27; pp. 1533–1551.

Kuhne et al., "Flow Cytometric Evaluation of Platelet Activation in Blood Collected into ECTA vs. Diatube–H, a Sodium Citrate Solution Supplemented with Theophylline, Adenosine, and Dipyridamole", American Journal of Hematology 50:pp. 40–45 (1995).

Karrenbrock et al., "A comparative study of the effects of SIN–1, sodium nitroprusside and nitrates on inhibition of platelet aggregation and activation of soluble guanylate–cyclase in human platelets (in French)", Path Biol, 1987, 35 No. 2 bis, pp. 251–254.

Siffert et al., "Inhibition of Platelet Aggregation by Amiloride", Thrombosis Research 44, pp. 235–240, 1986.

Becker et al., "Effect of Prostaglandin E1 on Harvesting of Plates from Refrigerated Whole Blood" J. Lab. Clin. Med. (1974) 83(2), pp. 304–9, abstract.

*Primary Examiner*—Sandra E. Saucier
*Attorney, Agent, or Firm*—Arnold White & Durkee

[57] ABSTRACT

This invention provides a method for prolonging the preservation of human blood platelets at reduced temperatures. The method uses an inhibitor system that enables blood platelets to maintain their discoid shape and retain their functional integrity during storage. This is accomplished by interrupting normal platelet function during storage, so as to help keep platelets from activating and losing their shape. Before using the platelets in a transfusion, they are returned to their normal functional level by washing the inhibitor system away from the platelets. In particular, compositions comprising amiloride, adenosine and sodium nitroprusside are disclosed.

14 Claims, No Drawings

COMPOSITION COMPRISING THREE PLATELET LESION INHIBITORS FOR PLATELET STORAGE

This is a continuation-in-part of a divisional application Ser. No. 08/844,021 filed on Apr. 18, 1997 now abandoned which is a divisional of application Ser. No. 08/326,036 filed Oct. 19, 1994 now issued as U.S. Pat. No. 5,622,867.

The U.S. Government has a nonexclusive, non-transferable, irrevocable paid-up license to practice or have practiced this invention for or on its behalf as provided for by the terms of Contract Number DAMD 17-91-C-1107 awarded by the U.S. Department of the Army.

BACKGROUND OF THE INVENTION

1. Field of the Invention

This invention relates to a method for extending the shelf-life of human blood platelets. The invention relates particularly to a reversible inhibitor system and method that inhibits platelets from biologically activating during storage at refrigeration temperatures (4° C.) or freezer temperatures (−80° C.), but leaves platelets with the ability to resume normal reactions once the inhibitor system is removed. The composition and method of this invention enables storage of platelets at cryo-temperatures with recovery of function at a level previously impossible to achieve.

2. Description of Related Art

Platelet transfusions are frequently used to treat patients. Not only are platelet transfusions given to casualty victims suffering from massive blood loss, but also to patients undergoing chemotherapy. Chemotherapy reduces the number of a patient's platelets, and also causes the platelets that are present to function defectively. For example, with thrombocytopenia, a patient has a decreased number of platelets caused by bone marrow suppression, whereas a patient with hemorrhagic myocarditis may have platelets that have been rendered functionally defective by chemotherapy. Platelet transfusions are used to increase the number of platelets to treat conditions such as thrombocytopenia, and to replace functionally defective platelets in treating hemorrhagic myocarditis.

Blood platelets should be stored at the lowest temperature possible to reduce metabolic function and contaminant growth. Currently, platelets are stored for up to 5 days at 22° C. This storage time is limited by a decrease in pH due to increased lactate associated with anaerobic metabolic activity. Storage at 22° C. is also limited by the potential for bacterial growth. Refrigeration offers advantages over 22° C. storage with respect to metabolic function, contamination, and pH stability. However refrigerated storage results in multiple inherent problems. First, platelets undergo a change from discoid shape to a spherical configuration after about 24 hours of refrigerated storage. Second, spontaneous aggregation is increased after 24 to 48 hours of refrigerated storage. Third, platelets stored at 4° C. fail to recover functional activity following the storage period. Finally, platelets which undergo a storage lesion at 4° C. are cleared from the circulation by the spleen following transfusion.

Goals for refrigerated platelet storage are to preserve a high number of platelets, lengthen the time that platelets may be preserved, maintain the functional integrity of platelets and ensure that their in vivo circulatory life span approaches normal limits.

Since fresh platelets have a shelf-life of only 3 to 5 days at 22° C. (room temperature), methods for extending platelet shelf-life would be beneficial. Unfortunately, despite a number of attempts to optimize platelet storage, progressive changes in cell shape (resulting in biological dysfunction) and permanent deterioration in subsequent aggregation potential continue to limit platelet storage. In addition, platelets develop a lesion with storage that causes them to be removed from the circulation, predominantly by the spleen during the first passage following transfusion. For instance, the typical life span of a normal platelet in the human body is approximately eight days. Prior art attempts to store platelets for extended periods of time result in the creation of lesion-modified platelets. Approximately 80% to 90% of the prior art storage platelets can be numerically recovered after storage, but only 20% to 35% remain active after the first circulatory flow through the spleen. This is because the spleen filters out the lesion-modified platelets. Use of the compositions and methods of this invention result in the same 80% to 90% numerically recovered as the prior art, but since lesion-modified platelets are not produced, 65% to 80% of the reactivated platelets should function biologically for the typical time in the human body. Several approaches such as reduced storage temperature, cryopreservation techniques, additives and artificial storage media yield an increased number of platelets following storage. However, the functional capacity and persistence in circulation of the platelets recovered by these methods is limited.

Blood banks and hospitals very much need a platelet storage system that provides an increased number of platelets after storage, but also prevents platelets from aggregating during storage and enables them to continue to retain the ability to react normally once they are transfused into a patient including the ability of platelets to persist in the circulation and not be cleared. This may be accomplished by a platelet storage system that: prevents platelets from aggregating during storage; enables platelets to regain the ability to react normally after removal from storage; and allows platelets to persist in circulation and avoid being cleared by the spleen.

Previous attempts to use platelet activation inhibitors have met with very limited success. This is primarily because the prior art teaching is limited to the use of a single inhibitor in an attempt to preserve platelet function. The single inhibitor system results in improved results over no inhibitor at all, but does not approach the unexpected results achieved using the compositions and methods of the subject invention. Prior methods for the use of single inhibitor systems are explained in Valeri, Feingold, and Marchionni, *A Simple Method for Freezing Human Platelets Using Dimethylsulfoxide and Storage at −80° C., Blood,* Vol. 43, No. 1 (January), 1974 and Bode, Holme, Heaton, and Swanson, *Extended Storage of Platelets in an Artificial Medium with the Platelet Activation Inhibitors Prostaglandin E. and Theophylline,* Vox Sang 1991:60;105–112.

For thrombocytopenic patients, platelets represent an important transfusable blood component for the control of bleeding. Under current guidelines, platelets can be stored for a maximum of 5 days at 20 to 24° C., thus creating an inventory control problem for hospitals and blood banks. This 5 day storage restriction at 22° C. is the result of concerns over the possibility of bacterial contamination during the collection process and the bacterial propagation that occurs during storage at this temperature. During 22° C. storage, platelets also experience a decline in functional activity known as storage lesion. The ability to store platelets for extended periods of time in a frozen state would aid in the management of these storage-associated problems. Unfortunately, cryopreservation of platelets, unlike red cells, is neither a simple nor effective method of storage. In fact, while cryopreservation of autologous platelets for patients prior to bone marrow ablation or for alloimmunized patients in remission is desirable, routine frozen storage of autologous platelets is not considered practical.

Currently, there are two AABB approved methods for platelet cryopreservation. The first requires 5% DMSO as a cryoprotectant. The procedure is labor intensive, requires a controlled-rate addition of a plasma/DMSO mixture and storage at −135° C., an unconventional temperature for routine blood bank storage. The second method requires 6% DMSO and a controlled-rate addition of a plasma/DMSO mixture. Storage is at the more conventional temperature of −80° C. Following thawing, both methods require a wash step prior to transfusion and platelets frozen using the 6% DMSO method must be transfused within 4 hours of being washed. Furthermore, the current cryopreservation methods cause significant damage to the platelets.

Following cryopreservation, a 15 to 22% loss of platelet cell number is seen together with a decrease in in vitro viability and an elevated level of lactate dehydrogenase in the supernatant. The thawed platelets also display a loss of their discoid shape and assume a spherical or balloon shape, which may result in clumping. Mean platelet volume of the cells is increased as is the expression of the activation marker P-Selectin. Functionally, the cryopreserved platelets show a loss of many critical in vitro activity parameters. Platelet aggregation in response to the agonists ADP, collagen, thrombin, epinephrine, arachidonic acid and adrenaline is decreased. The cryopreserved platelets display a reduced ability to release granule contents, including ATP and Thromboxane $B_2$, in response to agonists. In addition, in response to thrombin or collagen, the intracellular release of $Ca^{++}$, and the secretion of 5-hydroxytryptamine and platelet factor 4 is diminished. This effect is also reflected as a decrease in both the dense and a granule contents including serotonin, platelet factor 4 and β-thomboglobulin. Hypotonic shock response (HSR), which is a measurement of the platelets' ability to recover from a hypotonic insult, is considered a good determinate of in vitro viability. Following thaw, cryopreserved cells display a significant reduction in hypotonic shock response. Furthermore, the cryopreserved platelets displayed a 50% decrease in adhesion to the subendothelial matrix of rabbit aorta, as compared to fresh or 5 day 22° C. stored platelets, using a Baumgartner model.

This loss of in vitro functional activity is also reflected in the cryopreserved platelets' in vivo parameters. Following infusion, the in vivo 1 to 2 hour recovery of $^{51}$Cr-labeled cyropreserved platelets ranges from 30% to 40% as assessed in multiple studies. Taken in conjunction with the loss from the freeze-thaw process and the post-thaw wash step, the final in vivo recovery can be as low as 18% of the original fresh platelet population. Interestingly, the platelets that do remain in circulation display a normal circulatory lifespan of approximately 8 days. In vivo analysis of unit-size transfusions of cryopreserved platelets demonstrates that these cells achieve about 46% to 65% improvement in corrected count increments (CCI) as compared to fresh units. The surviving cryopreserved platelets do retain the ability to exert hemostatic properties. In both an aspirin treatment model with healthy recipients and in thrombocytopenic patients, the cryopreserved platelets showed some correction of bleeding time, though to a lesser degree than fresh cells. Thus, it has been determined that it takes about 2.5 units of cryopreserved platelets to equal one unit of fresh platelets.

The instant invention addresses the above noted problems of platelet storage, reactivation, and long term functional effectiveness of blood platelets. Further the present invention achieves unexpected and unobvious results in the preservation of blood platelets through treating with the compositions and methods of this invention and which previously would have been considered impossible.

SUMMARY OF THE INVENTION

The present invention is generally directed to compositions and methods for prolonging the preservation of human blood platelets. The compositions and methods use an inhibitor system that enables blood platelets to maintain their discoid shape and retain their functional integrity during prolonged storage. The unexpected and unobvious results of the present invention are accomplished by inhibiting normal platelet function, so as to help keep platelets from biologically activating during storage.

The composition of the present invention includes an inhibitor system that is made up of second messenger effectors. This second messenger inhibitor system functions through one or more of the following pathways: cyclic adenosine monophosphate (cyclic AMP), sodium channel, cyclic guanosine monophosphate (cyclic GMP), cyclooxygenase, lipoxygenase, phospholipase, the calcium cascade, protease and proteinase, and membrane modification. More specifically, special agents or combinations of agents may be used for each of the pathways. For example, adenosine, iloprost, prostacyclin and $PGE_2$ act to inhibit activation through stimulation of the cyclic AMP pathway. Amiloride and amiloride analogues act to inhibit activation through inhibition of the sodium channel. Sodium nitroprusside and L-arginine act to inhibit activation through stimulation of the cyclic GMP pathway. Aspirin, dipyridamole, flurbiprofen, and ticlopidine act to inhibit activation through inhibition of the cyclooxygenase pathway. Aspirin and ticlopidine act to inhibit platelet activation through inhibition of the lipoxygenase pathway. Quinacrine acts to inhibit platelet activation through the inhibition of the phospholipase pathway. Calcium acts to promote platelet activation through the calcium cascade. Protease and or proteinases act to inhibit platelet aggregation through the inhibition of surface receptor changes. Amantadine, ajoene, heparin, ticlopidine, and/or pentoxifylline act as membrane modifiers.

The inhibitor systems described above are preferred for storage at low temperatures, i.e. from 2 to 8° C. When subzero storage temperatures (−20 to −135° C.) are used, it is beneficial to introduce a cryoprotective agent to the platelets before cryopreparation. Suitable cryoprotective agents include dimethyl sulfoxide, maltodextrins, dextran, hydroxyethyl starch and glucose, although other cryoprotective agents may also be used. Cryoprotective agents may be used individually or in combination.

In one embodiment for preserving human platelets the method includes drawing whole human blood via venipuncture into an evacuated tube containing an anticoagulant. The blood is centrifuged to isolate platelet-rich plasma from the blood. The platelet-rich plasma is centrifuged to separate platelet-poor plasma from the platelet pellet, which is the concentrated platelets left after centrifuging and decanting the plasma. An inhibitor system is added to the platelet-poor plasma. This inhibitor system may include three or more platelet lesion inhibitors selected from effectors of the cyclic AMP second messenger system, inhibitors of the sodium channel, effectors of the cyclic GMP second messenger system, inibitors of the cyclooxygenase pathway, inhibitors of the lipoxygenase pathway, inhibitors of the phospholipase pathway, inhibitors of the calcium cascade, proteases, proteinases, membrane modifiers and combinations thereof. In one preferred embodiment the three or more platelet lesion inhibitors are present in a concentration so as to prolong the in vitro preservation of the bioactive blood platelets and even more preferably have concentrations from 0.1 mM to 10 mM, preferably about 1 mM amiloride in dimethyl sulfoxide (DMSO); from about 2.5 $\mu$M to about 250 $\mu$M, preferably about 25 $\mu$M sodium nitroprusside (NaNP) in phosphate buffered saline; from about 10 $\mu$M to about 1 mM, preferably about 0.1 mM adenosine in phosphate buffered saline; from about 10 mM to about 1 $\mu$M, preferably about 0.1 $\mu$M quinacrine in phosphate buffered saline; from about 2 $\mu$M to about 200 $\mu$M, preferably 20 $\mu$M dipyridamole in DMSO; from about 0.5 mM to about 5 mM, preferably 1.5 mM ticlopidine in DMSO; and from about 5 units/ml to about 200 units/ml, preferably 20 units/ml heparin in phosphate buffered saline. The platelet pellet is gently resuspended in the platelet-poor plasma/inhibitor system mixture. The mixture is then placed in a platelet storage container and stored at (20° to 8° C.) without agitation. An alternative method of adding the inhibitors is to create a suspension of the inhibitors described but without the addition of DMSO. The suspension is then lyophilized. At the time of addition, the lyophilized powder of inhibitors is rehydrated with platelet poor plasma and then added to the platelet pellet.

In another embodiment, the blood platelet stored at cryogenic temperatures, that is to say −20 to −135° C. In one such embodiment the inhibitor system is similar to that utilized to store blood platelets at 4° C. In another, preferred embodiment the inhibitor system includes amiloride, adenosine and sodium nitroprusside. In either case a cryoprotective agent is included in the formulation of the inhibitor system. In one such embodiment, the cryoprotective agent, dimethyl sulfoxide, makes up a part of the inhibitor system used for −20 to −135° C. storage, and the platelet storage container must be one suitable for storage at −20 to −135° C.

Thus one embodiment of the present invention is a platelet storage composition including a plasma composition and three or more platelet lesion inhibitors. In such an embodiment the platelet lesion inhibitors should be present at a concentration so as to permit in vivo preservation of bioactive platelets.

In yet another embodiment of the present invention, a blood platelet composition is formed that includes bioactive blood platelets, blood plasma or a plasma composition or a combination of blood plasma and blood plasma composition and three or more platelet lesion inhibitors.

Another embodiment is directed to a human blood platelet composition including bioactive human blood platelets, human blood plasma or a plasma composition or a combination of human blood plasma and blood plasma composition. The composition further includes three or more platelet lesion inhibitors selected so that a cyclic AMP second messenger system is selected from adenosine, iloprost, prostacyclin, PGE$_2$, forskolin, cholera toxin, isoproterenol, 8-bromo cAMP, dibutyl cAMP, theophylline, isobutylmethyl xanthine, thyrotropin, and auranofin; a inhibitor acting through the sodium channel is selected from amiloride, amiloride analogues, bepridil, flecainide, saxitoxin, benzamil and prajnalium; a inhibitor acting through the GMP pathway is selected from sodium nitroprusside, L-arginine, nitrous oxide, SIN-1, SIN-1A, atrial natriuretic factor, vasopressin, oxytocin, and glyceryl trinitrate; a inhibitor acting through the cyclooxygenase pathway is selected from aspirin, dipyridamole, flurbiprofen, ticlopidine, ketoprofen, ibuprofen, indomethacin, sulfinpyrazone, guanabenz, ursolic acid and benzohydroquinone; a inhibitor acting through the lipoxygenase pathway is selected from aspirin, ticlopidine, ursolic acid, unbelliferone, 5,8,11,14 eicosatetraynoic acid and esculetin; a inhibitor acting through the phospholipase pathway is selected from quinacrine and mepacrine; a inhibitor acting through the calcium cascade is selected from protein kinase C effectors, calcium channel blockers, calcium concentration modifiers, calmodulin effectors, calcium ionophores and ATPase stimulators; a inhibitor protease or proteinase is selected from heparin and apoprotinin; and, a membrane modifier is selected from amantadine, heparin, ticlopidine, pentoxifylline and ajoene. The three or more platelet lesion inhibitors are present in a concentration so as to prolong the in vitro preservation of the bioactive blood platelets.

DETAILED DESCRIPTION OF THE PREFERRED EMBODIMENTS

Activation during storage is undesirable. However, platelets must retain the ability to activate when they are taken out of storage to function normally for transfusion purposes. When the platelets are removed from storage, the inhibitor system of this invention may be washed from the platelets, which allows them to return very closely to their normal level of activity. This washing step can be achieved in vitro by mechanical washing or by a dilution effect from direct transfusion.

There are three platelet activity parameters that are measured to determine whether platelets have retained their functional ability after storage. These parameters are useful when they are compared to the same parameters for fresh platelets. Additionally, the platelet activity parameters for platelets stored with different inhibitor mixtures may be compared to determine which inhibitor combinations yield more functional platelets after storage. The tests used to measure platelet activity parameters preserved by this invention are: platelet number, hypotonic stress response, collagen-induced aggregation and adenosine diphosphate (ADP)-induced aggregation. In addition, measurement of granule release yields important information about the integrity of the platelets during storage.

Hypotonic stress response is an assay used to determine if platelets have retained metabolic viability. This assay is a photometric measurement of the platelets' ability to overcome the addition of a hypotonic solution. This activity reflects cell function (i.e. a functional membrane water pump) and is indicative of platelet recovery following storage. Hypotonic stress response has been demonstrated to be an important indicator of platelets' ability to survive in circulation following transfusion. Consequently, hypotonic stress response represents a crucial parameter for evaluating platelet biochemistry following storage.

Potential for aggregation is another feature that demonstrates whether blood platelets have maintained their functional integrity during storage. This potential is measured by using ADP and collagen to induce aggregation. An agonist is an agent that binds to a receptor and initiates a certain response. In an agonist-induced aggregation, the aggregation or clumping is the response. The agonists, ADP and collagen, are used to induce aggregation to determine if platelets have retained their ability to aggregate. In addition, when performing aggregation responses one can detect the presence of spontaneous aggregation, that is the platelets adhering to each other without the addition of an agonist. The occurrence of spontaneous aggregation has been correlated with removal of platelets from the circulation and hence have short survival times.

The inhibitor system of this invention is based on the application of specific second messenger effectors, which interact with the platelets and stabilize the cells to resist loss of viability and functional activity during storage at 4° C. and at −80° C.

In one embodiment, specific modifiers that make up the preferred seven component inhibitor system are amiloride, adenosine, sodium nitroprusside, quinacrine, dipyridamole, ticlopidine and heparin. These modifiers are added to the platelet pellet following dilution (from a 100-fold concentrate) into autologous platelet-poor plasma. Each of these modifiers affects a different specific second messenger pathway. Amiloride is a potassium conserving diuretic, employed medicinally in the treatment of hypertension. In this invention, amiloride acts as an inhibitor of the platelet Na+-H+ exchanger. Adenosine is used medicinally to restore normal sinus rhythm in patients. In this invention, adenosine stimulates the production of cyclic AMP. Sodium nitroprusside relaxes smooth muscle thus serving as a vasodilator, medicinally. In this invention, sodium nitroprusside stimulates the production of cyclic GMP. Dipyridamole is employed medicinally as a platelet adhesion inhibitor. In this invention, dipyridamole acts as an inhibitor of cyclooxygenase and lipoxygenase enzymes of the arachidonic acid cascade. Quinacrine is used in the treatment to eradicate intestinal cestodes. In this invention, quinacrine serves as a phospholipase A2 inhibitor. Medicinally, ticlopidine is used as a platelet aggregation inhibitor to reduce the risk of thrombotic strokes. In this invention, ticlopidine is used as an inhibitor of the arachidonic acid cascade. Heparin is employed medicinally as an anti-clotting agent in blood. In this invention, heparin is used to block fibrin binding.

All of the second messenger effectors have been demonstrated to inhibit agonist induced aggregation both separately and in combination with the others. More importantly, the inhibition is reversible following removal of the effector(s) by washing the platelets. Upon adding the second messenger effectors, both individually or in combination, platelets were less susceptible to storage lesions during storage at 2 to 8° C. or at −20 to −135° C. These cells also displayed normal aggregation physiology upon removal of the effector(s), they also did not display spontaneous aggregation and maintained a high hypotonic stress response.

In describing the chemicals which have shown utility as platelet lesion inhibitors, it must be understood that the actual chemicals mentioned together with functionally equivalent materials are intended to be within the scope of this invention. Chemicals that are known to applicants to have known or demonstrated utility as inhibitors have been specifically set forth in the instant application. However, it is intended that the scope of the application be extended to other finctionally effective chemicals, both existing chemicals and chemicals yet to be discovered.

Certain chemicals which are thought to be functionally equivalent materials for the inhibitor acting through the sodium channel are those selected from the group consisting of amiloride, amiloride analogues, bepridil, flecainide, saxitoxin, benzamil and prajnalium. Materials thought to be functionally equivalent to the inhibitor acting through the GMP pathway are selected from the group consisting of sodium nitroprusside, L-arginine, nitrous oxide, SIN-1, SIN-1A, atrial natriuretic factor, vasopressin, oxytocin, and glyceryl trinitrate. Functionally equivalent materials for the inhibitor acting through the cyclooxygenase pathway are selected from the group consisting of aspirin, dipyridamole, flurbiprofen, and ticlopidine, ketoprofen, ibuprofen, indomethacin, sulfmpyrazone, guanabenz, ursolic acid and benzohydroquinone. Functionally equivalent materials for the inhibitor component acting through the lipoxygenase pathway are selected from the group consisting of aspirin, ticlopidine, ursolic acid, unbelliferone, 5,8,11,14 eicosatetraynoic acid and esculetin. Finally, finctionally equivalent materials to the inhibitor acting through the calcium cascade are selected from the group consisting of protein kinase C effectors, calcium channel blockers, calcium concentration modifiers, calmodulin effectors, calcium ionophores and ATPase stimulators.

The shelf-life of blood platelets may be successfully extended by storing the cells at. 4° C. with the inhibitor system of this invention. When platelets that were stored at 4° C. for 10 days were analyzed for post-storage activity, as compared to the activity of fresh platelets, the percentage of the cells' activity was as follows: 70% ADP-induced aggregation, 85% collagen-induced aggregation, 65% hypotonic stress response and >95% recovery of cell number. These results compare favorably to conventional storage of platelets at 22° C. following 5days of storage which yielded 55% ADP-induced aggregation, 80% collagen-induced aggregation 50% hypotonic stress response, as compared to fresh platelets.

To perform the 4° C. experiment, whole blood is drawn via venipuncture into blood bags containing the anti-coagulant acid-citrate dextrose as prescribed by the procedures and protocols of the American Association of Blood Banks and performed by a blood procurement agency. To perform small scale experimentation, whole blood can also be drawn into 6 milliliter evacuated tubes and processed by the same protocols as with the blood bags. The blood bags are centrifuged at 2000 × g for 3 minutes to separate the red blood cells from the platelets and the plasma. The platelet-rich plasma is isolated by expression into a connected platelet storage bag followed by a second centrifugation at 5000 × g for 5 minutes to pellet the platelets. The platelet-poor plasma is expressed into a plasma storage bag, while the resulting platelet pellet, with approximately 50 to 60 milliliters of plasma is left for one hour at 22° C. as prescribed by blood banking procedures. Following the incubation, the platelet preparation is resuspended in the residual plasma by gentle shaking. In the small scale experiments in 6 milliliter tubes, an equivalent volume of plasma is left on the platelet pellet and the platelet sample is resuspended.

An inhibitor system solution is prepared as follows: A solution of reagents is prepared in DMSO containing 100 mM amiloride, 150 mM ticlopidine, and 2 mM dipyridamole. A solution of reagents is prepared in phosphate buffered saline containing 2.5 mM sodium nitroprusside, 10 mM adenosine, 10 $\mu$M quinacrine, and 2,000 units/ml of heparin. The concentration of the inhibitor system reagents in these mixtures is 100-fold the final concentration needed in the platelet preparation to achieve effective storage at 4° C. The inhibitor solutions are added to the platelet concentrate at a $\frac{1}{100}$ volume of the total platelet preparation volume via a direct injection through a sterile port. The order of addition of the DMSO solution and the phosphate-buffered saline solution is not believed essential to the practice of the invention. The final concentration of the inhibitor reagents in the platelet preparation is as follow: amiloride (1 mM), adenosine (0.1 mM), sodium nitroprusside (25 $\mu$M), dipyridamole (20 $\mu$M), quinacrine (0.1 $\mu$M), ticlopidine (1.5 mM), and heparin (20 units/ml). The platelet preparation in a standard platelet storage bag is placed at 4° C. without agitation. The platelet composition with the inhibitor system can be directly transfused following storage.

Alternatively the combination of inhibitors can be added to the platelet pellet in the absence of DMSO. This can be achieved in two ways. The combination of inhibitors can be processed to a suspension by sonication. This sonicated suspension can then be used directly as described above. Alternatively, the sonicated suspension can be lyophilized and stored as a lyophilized powder. Upon use, the powder is rehydrated with an appropriate volume of platelet poor plasma and added to the platelet pellet as described above. Using either method, the final concentration of additives (excepting the absence of DMSO) is the same as described above.

A second use of this invention involves the storage of platelets at −20 to −135° C. The addition of the inhibitor solution system of this invention to the platelet pellet effectively stabilizes the platelets thus allowing the cells to be successfully cryopreserved and stored at −20 to −135° C.

Storing platelets at −20 to −135° C. requires the addition of a cryoprotective agent. As part of the process of this invention dimethyl sulfoxide (DMSO) serves as the cryoprotectant. DMSO is a polar molecule which penetrates the cell membrane and serves to preserve cell viability during the cryopreparation process. DMSO functions in this invention to stabilize the platelets allowing recovery of functionally active platelets after storage at −20 to −135° C. After long term storage of platelets (>100 days) that were cryopreserved with the inhibitor system of this invention, the number of cells recovered and the functional activity of the platelets was compared to that of fresh platelets. More than 95% of the cryopreserved cells were recovered and these platelets displayed a functional activity of 55% ADP-induced aggregation, 65% collagen aggregation and 50% hypotonic stress response. These results compare favorably to conventionally stored platelets following 5 day storage at 22° C. In addition, other cryoprotecting agents may be substituted for the DMSO in this protocol; these include maltodextrin, dextran, hydroxylethyl starch, and glucose, either individually or in combination.

To process platelets for the use of the inhibitor storage system of this invention, a platelet concentrate is generated as prescribed by blood banking procedures and detailed in the 4° C. storage section (B). An inhibitor system solution is prepared as followed: A solution of reagents is prepared in DMSO containing 100 mM amiloride, 150 mM ticlopidine, and 2 mM dipyridamole. A solution of reagents is prepared in phosphate buffered saline containing 2.5 mM sodium nitroprusside, 10 mM adenosine, 10 $\mu$M quinacrine, and 2,000 units/ml of heparin. The concentration of the inhibitor system reagents in these mixtures is 100-fold the final concentration needed in the platelet preparation. The inhibitor solutions are added to the platelet concentrate at a $\frac{1}{100}$ volume of the total platelet preparation volume via a direct injection through a sterile port. The order of addition of the DMSO solution and the phosphate-buffered saline solution is irrelevant. The final concentration of the inhibitor reagents in the platelet preparation is as follows: amiloride (1 mM), adenosine (0.1 mM), sodium nitroprusside (25 $\mu$M), dipyridamole (20 $\mu$M), quinacrine (0.1 $\mu$M), ticlopidine (1.5 mM), and heparin (20 units/ml). In addition, DMSO is added directly to the platelet preparation via injection through a sterile port to a final concentration of between 1% and 6%, preferably 2%. The platelet storage bag, compatible with storage at −20 to −135° C., is placed in a standard freezing cassette followed by placement in a −20 to −135° C. freezer.

Following storage of the platelets at −20 to −135° C. with the inhibitor system of this invention, the platelet preparation is removed from the −20 to −135° C. freezer and directly placed in a 37° C. water bath until the entire preparation is thawed. The platelet concentrate with the inhibitor system can be directly transfused following the thawing procedure. Alternatively, the platelet preparation can be centrifuged to pellet the platelets, thus removing the DMSO component of the cryopreservation solution. These platelets can then be resuspended in autologous plasma and directly transfused.

A platelet storage composition comprising a plasma composition including three or more platelet lesion inhibitors, the platelet lesion inhibitors being present at a concentration so as to permit in vitro preservation of bioactive platelets. As the term is used herein and in the claims, "plasma composition" is intended to mean a pharmacologically inert fluid into which the bioactive blood platelets may be suspended and which does not adversely affect the preservation abilities of the compositions disclosed herein, examples include physiological saline, blood plasma, blood plasma substitutes, combinations of these and the like. The three or more platelet lesion inhibitors may be selected from: effectors of the cyclic AMP second messenger system, inhibitors of the sodium channel, effectors of the cyclic GMP second messenger system, inhibitors of the cyclooxygenase pathway, inhibitors of the lipoxygenase pathway, inhibitors of the phospholipase pathway, inhibitors of the calcium cascade, proteases, proteinases, membrane modifiers and combinations thereof, In one preferred embodiment the cyclic AMP second messenger system is selected from adenosine, iloprost, prostacyclin, $PGE_2$, forskolin, cholera toxin, isoproterenol, 8-bromo cAMP, dibutyl cAMP, theophylline, isobutylmethyl xanthine, thyrotropin, and auranofin; the inhibitor acting through the sodium channel is selected from amiloride, amiloride analogues, bepridil, flecainide, saxitoxin, benzamil and prajnalium; the inhibitor acting through the GMP pathway is selected from sodium nitroprusside, L-arginine, nitrous oxide, SIN-1, SIN-1A, atrial natriuretic factor, vasopressin, oxytocin, and glyceryl trinitrate; the inhibitor acting through the cyclooxygenase pathway is selected from aspirin, dipyridamole, flurbiprofen, ticlopidine, ketoprofen, ibuprofen, indomethacin, sulfinpyrazone, guanabenz, ursolic acid and benzohydroquinone; the inhibitor acting through the lipoxygenase pathway is selected from aspirin, ticlopidine, ursolic acid, unbelliferone, 5,8,11,14 eicosatetraynoic acid and esculetin; the inhibitor acting through the phospholipase pathway is selected from quinacrine and mepacrine; the inhibitor acting through the calcium cascade is selected from protein kinase C effectors, calcium channel blockers, calcium concentration modifiers, calmodulin effectors, calcium ionophores and ATPase stimulators; the inhibitor protease or proteinase is selected from heparin and apoprotinin and the membrane modifier is selected from amantadine, heparin, ticlopidine, pentoxifylline and ajoene. The platelet storage composition of the present embodiment may further include a cryoprotective agent, the cryoprotective agent being selected from dimethyl sulfoxide, maltodextrin, dextran, hydroxylethyl starch, glucose and combinations thereof. The cryoprotective agent is preferably dimethyl sulfoxide and has a concentration of about 0.5% to about 10% Preferably the dimethylsulfoxide has a concentration of about 0.5% to about 6% and more preferably a concentration of about 2%.

In yet another embodiment of the present invention, a blood platelet composition is formed that includes bioactive blood platelets, blood plasma or a plasma composition or a combination of blood plasma and blood plasma composition and three or more platelet lesion inhibitors. Preferably the platelet lesion inhibitors are selected form from effectors of the cyclic AMP second messenger system, inhibitors of the sodium channel, effectors of the cyclic GMP second messenger system, inhibitors of the cyclooxygenase pathway, inhibitors of the lipoxygenase pathway, inhibitors of the phospholipase pathway, inhibitors of the calcium cascade, proteases, proteinases, membrane modifiers and combinations thereof, wherein the three or more platelet lesion inhibitors are present in a concentration so as to prolong the in vitro preservation of the bioactive blood platelets. In a more preferred embodiment, the cyclic AMP second messenger system is selected from adenosine, iloprost, prostacyclin, $PGE_2$, forskolin, cholera toxin, isoproterenol, 8-bromo cAMP, dibutyl cAMP, theophylline, isobutylmethyl xanthine, thyrotropin, and auranofin; the inhibitor acting through the sodium channel is selected from amiloride, amiloride analogues, bepridil, flecainide, saxitoxin, benzamil and prajnalium; the inhibitor acting through the GMP pathway is selected from sodium nitroprusside, L-arginine, nitrous oxide, SIN-1, SIN-1A, atrial natriuretic factor, vasopressin, oxytocin, and glyceryl trinitrate; the inhibitor acting through the cyclooxygenase pathway is selected from aspirin, dipyridamole, flurbiprofen, ticlopidine, ketoprofen, ibuprofen, indomethacin, sulfinpyrazone, guanabenz, ursolic acid and benzohydroquinone; the inhibitor acting through the lipoxygenase pathway is selected from aspirin, ticlopidine, ursolic acid, unbelliferone, 5,8,11,14 eicosatetraynoic acid and esculetin; the inhibitor acting through the phospholipase pathway is selected from the group consisting of quinacrine and mepacrine; the inhibitor acting through the calcium cascade is selected from protein kinase C. effectors, calcium channel blockers, calcium concentration modifiers, calmodulin effectors, calcium ionophores and ATPase stimulators; the inhibitor protease or proteinase is selected from heparin and apoprotinin; and, the membrane modifier is selected from amantadine, heparin, ticlopidine, pentoxifylline and ajoene. It is preferred that when the blood platelets are being prepared for storage a cryogenic temperatures that the three or more platelet lesion inhibitors include amiloride, adenosine sodium nitroprusside and a cryoprotective agent, the cryoprotective agent being selected from dimethyl sulfoxide, maltodextrin, dextran, hydroxylethyl starch, glucose and combinations thereof. The cryoprotective agent may have a concentration from about 0.5% to about 10% in one preferred embodiment. In these embodiments, the blood platelet composition should have concentrations of the three or more platelet lesion inhibitors so that upon in vitro preservation of the bioactive blood platelets the bioactive blood platelets exhibit an increased in vitro functional activity when compared to bioactive blood platelets preserved under the same conditions but in the absence of the platelet lesion inhibitors. As previously noted, the prolonged storage of bioactive blood platelets should be carried out at a temperature below the blood platelets' normal physiological temperature. In one embodiment, that temperature is from about 10° C. to about 0° C. In another embodiment the temperature below the blood platelets' normal physiological temperature is less than about 10° C.

Alternatively, another embodiment of the present invention may be a human blood platelet composition including bioactive blood platelets; human blood plasma or a plasma composition, or a combination of human blood plasma and blood plasma composition and three or more platelet lesion inhibitors. Those platelet lesion inhibitors may be selected so that a cyclic AMP second messenger system is selected from adenosine, iloprost, prostacyclin, $PGE_2$, forskolin, cholera toxin, isoproterenol, 8-bromo cAMP, dibutyl cAMP, theophylline, isobutylmethyl xanthine, thyrotropin, and auranofin; a inhibitor acting through the sodium channel is selected from amiloride, amiloride analogues, bepridil, flecainide, saxitoxin, benzamil and prajnalium; a inhibitor acting through the GMP pathway is selected from sodium nitroprusside, L-arginine, nitrous oxide, SIN-1, SIN-1A, atrial natriuretic factor, vasopressin, oxytocin, and glyceryl trinitrate; a inhibitor acting through the cyclooxygenase pathway is selected from aspirin, dipyridamole, flurbiprofen, ticlopidine, ketoprofen, ibuprofen, indomethacin, sulfinpyrazone, guanabenz, ursolic acid and benzohydroquinone; a inhibitor acting through the lipoxygenase pathway is selected from aspirin, ticlopidine, ursolic acid, unbelliferone, 5,8,11,14 eicosatetraynoic acid and esculetin; a inhibitor acting through the phospholipase pathway is selected from the group consisting of quinacrine and mepacrine; a inhibitor acting through the calcium cascade is selected from protein kinase C effectors, calcium channel blockers, calcium concentration modifiers, calmodulin effectors, calcium ionophores and ATPase stimulators; a inhibitor protease or proteinase is selected from heparin and apoprotinin; and, a membrane modifier is selected from amantadine, heparin, ticlopidine, pentoxifylline and ajoene. The three or more platelet lesion inhibitors are present in a concentration so as to prolong the in vitro preservation of the bioactive blood platelets. In one preferred embodiment, the three or more platelet lesion inhibitors include amiloride, adenosine and sodium nitroprusside. Even more preferably, the amiloride has a concentration from about 0.1 mM to about 10 mM, the adenosine has a concentration from about 10 $\mu$M to about 1 mM and the sodium nitroprusside has a concentration from about 2.5 $\mu$M to about 250 $\mu$M. The composition may further include a cryoprotective agent, the cryoprotective agent being selected from dimethyl sulfoxide, maltodextrin, dextran, hydroxylethyl starch, glucose and combinations thereof. The preferred embodiment includes a cryoprotective agent which may be dimethyl sulfoxide in a concentration from about 0.5% to about 10%.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

The following example describes results of experiments testing prolonged storage at 4° C. Six tubes of whole blood were drawn via venipuncture of the antecubital vein into 6 milliliter draw evacuated tubes containing acid-citrate dextrose anticoagulant. The tubes containing whole blood were centrifuged at 250×g for 12 minutes. Platelet-rich plasma was isolated. The platelet-rich plasma was centrifuged at 950×g for 20 minutes. All the platelet-poor plasma was removed from the pellet. Solutions were added to the platelet-poor plasma that resulted in the following final concentrations: 1 mM amiloride; 25 $\mu$M sodium nitroprusside (NaNP); 0. mM adenosine in phosphate buffered saline; 0.1 $\mu$M quinacrine; 20 $\mu$M dipyridamole; 1.5 mM ticlopidine; 20 units/ml heparin and 1% DMSO. The platelet-poor plasma containing the solutions was returned to the platelet pellet to a volume of 1/10 of the original platelet-rich volume. The pellet was gently resuspended and the mixture was transferred to a platelet storage bag. The platelet bag with the mixture was stored at 4° C. without agitation. Results of the Above Method After 10 Day Storage at 4° C.

Following ten (10) days storage at 4° C. in standard platelet storage bags, the platelets were warmed to room temperature and diluted with autologous plasma to the original platelet-rich plasma volume. The platelets were analyzed for post-storage activity as compared to the activity of fresh platelets. The results of the activity profile are as follows:

ADP-Induced Aggregation–70%
Collagen-Induced Aggregation–85%
Hypotonic Stress Response–65%
Platelet Cell Number Recovery–95%

EXAMPLE 2

The following example describes results of experiments testing prolonged storage of platelets at 4° C. with combinations of three second messenger effectors. Platelets were harvested from whole blood preparation by centrifugation. The resulting platelet population was divided into aliquots and various combinations of effectors were added to each sample followed by refrigeration at 4° C. Following storage, the platelets were removed from 4° C. refrigeration, washed to remove the inhibitor agents, and evaluated for the retention of in vitro functional activity by testing ADP-induced aggregation and hypotonic shock response (HSR). The samples were treated as follows prior to the 4° C. storage:

1. Control, no treatment
2. amiloride (1 mM), adenosine (0.1 mM) and sodium nitroprusside (25 $\mu$M)
3. DMSO (1%), adenosine (0.1 mm) and sodium nitroprusside (25$\mu$M)
4. amiloride (0.1 mM), sodium nitroprusside (25 $\mu$M), dipyridamole (40 $\mu$M)
5. adenosine (0.1 mM), sodium nitroprusside (25 $\mu$M), dipyridamole (40 $\mu$M)
6. amiloride (0.25mM), dipyridamole (40 $\mu$M), sodium nitroprusside (25 $\mu$M)

The retention of functional activity for the treated platelets following 4° C. storage is displayed in TABLE 1.

TABLE 1

Storage of Platelets at 4° C. with Three Component Mixture of Effects

| Sample | Day 1 | | Day 5 | |
|---|---|---|---|---|
| | ADP aggregation | HSR | ADP aggregation | HSR |
| Control | 12 | 18 | 9 | 7 |
| amiloride adenosine; sodium nitroprusside | 69 | 61 | 35 | 47 |
| DMSO; adenosine; sodium nitroprusside | 20 | n.d.* | 26 | n.d. |
| amiloride; adenosine; dipyridamole | 24 | 57 | 21 | 40 |
| adenosine; sodium nitroprusside, dipyridamole | 43 | 58 | 39 | 26 |
| amiloride; sodium nitroprusside; dipyridamole | 42 | 59 | 39 | 42 |

*not determined

EXAMPLE 3

The following example describes results of experiments to test the prolonged storage of platelets at 4° C. with a effector mixture comprised of four components. Platelets were harvested from whole body by centrifugation. The resulting platelet population was divided into aliquots and treated with various combinations of second messenger effectors followed by storage at 4° C. Following the refrigeration, the platelet samples were washed and tested for the retention of functional activity by measuring against-induced aggregation and hypotonic shock response (HSR). The platelet samples were treated as follows prior to the 4° C. storage:

1. Control, no treatment
2. amiloride (1 mM), adenosine (0.1 mM) and sodium nitroprusside (25 $\mu$M), quinacrine (0.5 $\mu$M)
3. amiloride (1 mM), adenosine (0.1 mM) and sodium nitroprusside (25 $\mu$M), dipyridamole (0.1 mM)
4. amiloride (1 mMO, adenosine (0.1 mM) and sodium nitroprusside (25 $\mu$M), flurbiprofen (1 $\mu$M)
5. amiloride (1 mMO, adenosine (0.1 mM) and sodium nitroprusside (25 $\mu$M), ticlopidine (5 mM)
6. amiloride (1 mM), adenosine (0.1 mM) and sodium nitroprusside (25 $\mu$M), heparin (6.5 $\mu$g/ml)
7. amiloride (1 mM), adenosine (0.1 mM) and sodium nitroprusside (25 $\mu$M), ketorolac (10$\mu$M )

The retention of functional activity for the treated platelets following 4° C. storage is displayed in Table 2.

TABLE 2

Storage of Platelets at 4° C. with Four Component Mixture of Effectors

| Effector Combination | ADP aggregation | Day 1 Collagen aggregation | HSR | ADP aggregation | Day 5 Collagen aggregation | HSR |
|---|---|---|---|---|---|---|
| 1 | 12 | 12 | 8 | 0 | 0 | 0 |
| 2 | 88 | 94 | 82 | 47 | 94 | 31 |
| 3 | 53 | 94 | 79 | 41 | 82 | 15 |
| 4 | 0 | 19 | 15 | n.d.* | n.d. | n.d. |
| 5 | 27 | 100 | 82 | 13 | 63 | 79 |
| 6 | 35 | 98 | 81 | 20 | 57 | 43 |
| 7 | 47 | 59 | 23 | 24 | 29 | 10 |

*not determined

EXAMPLE 4

The following describes an example of the application of the inhibitor system of this invention to the storage of a whole unit platelet concentrate for extended period at 4° C. A whole unit of whole blood was drawn via venipuncture at the Gulf Coast Regional Blood Bank according to standard blood banking techniques into a sterile commercial blood collection system. The blood bag containing the whole blood was centrifuged according to standard blood banking procedures and the resultant platelet-rich plasma fraction was expressed into a standard platelet storage bag. The platelet-rich plasma was then centrifuged according to the blood banking protocol and the resultant platelet-poor plasma was expressed into a standard plasma storage bag. The resultant platelet pellet in the platelet storage bag still retains approximately 60 milliliters of plasma. This platelet concentrate is stored without agitation for one hour at 22° C. to allow the platelets to resuspend. A solution of inhibitors is prepared which contains the following: A solution of reagents is prepared in DMSO containing 100 mM amiloride, 150 mM ticlopidine, and 2 mM dipyridamole. A solution of reagents is prepared in phosphate buffered saline containing 2.5 mM sodium nitroprusside, 10 mM adenosine, 10 $\mu$M quinacrine, and 2,000 units/ml of heparin. The concentration of the inhibitor system reagents in these mixtures is 100 fold the final concentration needed in the platelet preparation. The inhibitor solutions are added to the platelet concentrate at a 1/100 volume of the total platelet preparation volume (approximately 0.6 milliliters) via a direct injection through a sterile port. The order of addition of the DMSO solution and the phosphate-buffered saline solution to the platelet concentrate is irrelevant. The final concentration of the inhibitor reagents in the platelet preparation is as follows: amiloride (1 mM), adenosine (0.1 mM), sodium nitroprusside (25 $\mu$M), dipyridamole (20 $\mu$M), quinacrine (0.1 $\mu$M), ticlopidine (1.5 mM), and heparin (20 units/ml). The platelet concentrate with the inhibitor solution is then stored at 4° C., without agitation. In parallel, as a means of comparison, a platelet concentrate unit was stored under the current blood banking method as follows: after the one hour incubation of the platelet concentrate to allow resuspension, the platelet preparation was stored at 22° C. with gentle agitation following standard blood banking procedures. In addition, a platelet concentrate preparation was stored at 4° C. without the inclusion of the inhibitor system. At various time intervals of storage, an aliquot of platelets was harvested from the conventionally stored preparation, the platelets stored at 4° C., and the platelets stored at 4° C. with the inclusion of the inhibitor solution of this invention. Platelets from these preparations were then analyzed for viability and functional activity of the cells. The results of this experiment are shown in TABLE 3. The data is expressed as a percentage of the viability and functional activity of fresh platelets at the time of acquisition.

TABLE 3

| | % of Fresh Platelets | | | | | |
|---|---|---|---|---|---|---|
| | ADP-Induced Aggregation | | Collagen-Induced Aggregation | | Hypotonic Stress Response | |
| Time (days) | 5 | 10 | 5 | 10 | 5 | 10 |
| 22° C. Storage | 32 | 28 | 67 | 42 | 35 | 57 |
| 4° C. Storage | 23 | 15 | 44 | 31 | 34 | 22 |
| Inhibitor System Storage | 54 | 58 | 89 | 83 | 86 | 65 |

In all tests of viability and functional activity, the platelet concentrate stored at 4° C. with the addition of the inhibitor system of this invention displayed. Higher recovery at day 10 than the conventionally stored platelets at day 5. Under current blood bank practices the maximum storage time for platelets is 5 days at 22° C.

EXAMPLE 5

The following example describes results of experiments testing prolonged storage of platelets via cryopreservation with multiple combinations of second messenger effectors. Platelets were harvested from whole blood preparation by centrifugation. The resulting platelet population was divided into aliquots and various combinations of effectors were added to each sample. The cryoprotectant DMSO was added to the treated samples and the platelet preparations were placed in a −80° C. freezer. In parallel, untreated, control platelets were cryopreserved using 6% DMSO only by the current methods. Following storage, the platelets were removed from the freezer, thawed in a 37° C. water bath, washed to remove the inhibitor agents, and evaluated for the retention of in vitro functional activity by testing ADP-induced aggregation, collagen-induced aggregation, and hypotonic shock response (HSR). The samples were treated as follows prior to cryopreservation.

1. Control, no treatment
2. amiloride (1 mM), adenosine (0.1 mM) and sodium nitroprusside (25 $\mu$M)
3. amiloride (1 mM), adenosine (0.1 mM) and sodium nitroprusside,(25 $\mu$M), heparin (6.5 $\mu$g/ml)
4. amiloride (1 mM), adenosine (0.1 mM) and sodium nitroprusside (25 $\mu$M), quinacrine (0.5 $\mu$M)
5. amiloride ($\mu$mM), adenosine (0.1 mM) and sodium nitroprusside (25 $\mu$M), dipyridamole (0.1 mM)
6. amiloride (1 mM), adenosine (0.1 mM) and sodium nitroprusside (25 $\mu$M), ketorolac (10 mM)

The results of this example are presented in TABLE 4.

TABLE 4

Storage of Platelets by Cryopreservation with Combination of Effectors Functional Activity Following Thaw

| Sample # | ADP-induced aggregation | Collagen-induced aggregation | HSR | Recovery of cell number |
|---|---|---|---|---|
| 1 | 33 | 50 | 36 | 59 |
| 2 | 67 | 100 | 54 | 84 |
| 3 | 63 | 88 | n.d.* | 95 |
| 4 | 75 | 63 | 68 | 87 |
| 5 | 67 | 100 | 71 | 91 |
| 6 | 76 | 82 | 80 | 81 |

*not determined

EXAMPLE 6

The following example describes an experiment to measure platelet activity after storage at −80° C. Six tubes of whole blood where drawn via venipuncture of the antecubital vein in 6 milliliter draw evacuated tubes containing acid-citrate dextrose anticoagulant. The tubes containing whole blood were centrifuged at 250×g for 12 minutes. Platelet rich plasma was isolated. The platelet rich plasma was centrifuged at 950×g for 20 minutes. A;; the platelet poor plasma was removed from the pellet. Solutions were added to the platelet poor plasma that resulted in the following concentration: 1 mM amiloride; 25 $\mu$M sodium nitroprusside; 0.1 mM adenosine; 0.1 $\mu$M quinacrine; 20 $\mu$M dipyridamole; 1.5 mM ticlopidine; 20 units/ml heparin and 6% dimethyl sulfoxide. The platelet poor plasma containing the solutions was returned to the platelet pellet to a volume of 1/10 the original platelet rich volume. The pellet was gently resuspended and the mixture was transferred to a platelet storage bag. The platelet storage bag with the mixture was stored at −80° C. in a standard red blood cell cassette designed for freezing.

Following a thaw, by directly placing the frozen platelet sample into a 37° C. water bath, the platelets were diluted with autologous plasma to the original platelet rich plasma volume. The platelets were analyzed for the post storage activity profiles as compared to fresh platelets and the results are as follows:

ADP-Induced Aggregation–50%

Collagen-Induced Aggregation–74%

Hypotonic Stress Response–78%

Platelet Cell Number Recovery–85%

EXAMPLE 7

The following describes an example of the application of the inhibitor system of this invention to the storage of a whole unit platelet concentrate for extended period at −80° C. via cryopreservation. A whole unit of whole blood was drawn via venipuncture at the Gulf Coast Regional Blood Bank according to standard blood banking techniques into a sterile commercial blood collection system. The blood bag containing the whole blood was centrifuged according to standard blood banking procedures and the resultant platelet-rich plasma fraction was expressed into a standard platelet storage bag. The platelet-rich plasma was then centrifuged according to the blood banking protocol and the resultant platelet-poor plasma was expressed into a standard plasma storage bag. The resultant platelet pellet in the platelet storage bag still retains approximately 60 milliliters of plasma. This platelet concentrate is stored without agitation for one hour at 22° C. to allow the platelets to resuspend. A solution of inhibitors is prepared which contains the following: A solution of reagents is prepared in DMSO containing 100 mM amiloride, 150 mM ticlopidine, and 2 mM dipyridamole. A solution of reagents is prepared in phosphate buffered saline containing 2.5 mM sodium nitroprusside, 10 mM adenosine, 10 µM quinacrine, and 2,000 units/ml of heparin. The concentration of the inhibitor system reagents in these mixtures is 100 fold the final concentration needed in the platelet preparation. The inhibitor solutions are added to the platelet concentrate at a 1/100 volume of the total platelet preparation volume (approximately 0.6 milliliters) via a direct injection through a sterile port. The order of addition of the DMSO solution and the phosphate-buffered saline solution to the platelet concentrate is irrelevant. The final concentration of the inhibitor preparation is as follows: amiloride (1 mM), adenosine (0.1 mM), sodium nitroprusside (25 µM), dipyridamole (20 µM), quinacrine (0.1 µM), ticlopidine (1.5 mM), and heparin (20 units/ml). In addition, DMSO is added to the platelet concentrate via injection through a sterile port to a final concentration of 6%. The platelet preparation in a standard freezer bag was put into a freezer cassette and placed at −80° C. In parallel, a platelet concentrate was cryopreserved according to the conventional blood banking methods, that is, the addition of 6% DMSO to the platelet concentrate followed by the placement of the platelet preparation at −80° C. in a freezer cassette. Following storage at −80° C. for 20 days, the platelet preparation was removed from the −80° C. freezer and placed directly into a 37° C. water bath. An aliquot of platelets was harvested and centrifuged to remove the DMSO. The platelet pellet-was resuspended in autologous plasma and the viability and functional activity of the cells was determined. The results of this experiment are shown in TABLE 5. The data is expressed as a percentage of the viability and functional activity of fresh platelets at the time of acquisition.

TABLE 5

| | % of fresh Platelets | | |
|---|---|---|---|
| | ADP-Induced Aggregation | Collagen-Induced Aggregation | Hypotonic Stress Response |
| Cryopreservation Conditions | | | |
| Conventional System | 0 | 13 | 7 |
| Inhibitor System | 58 | 76 | 61 |

The platelets stored via cryopreservation at −80° C., by employing the inhibitor system of this invention, display good recovery of viability and functional activity and thus are rendered capable to be effective following transfusion.

EXAMPLE 8

The following describes an example of the application of a three component inhibitor system of this invention to the storage of a whole unit platelet concentrate for extended period at −80° C. via cryopreservation. All of the reagents used for the storage of platelets were obtained from Sigma Chemical co., (St. Louis, Mo.). The aggregation agonists, ADP, collagen and ristocetin were purchased from Chronology Corp. (Havertown, Pa.). All of the reagents comprising the ThromboSol storage solution for cryopreservation (TC) (amiloride, adenosine, and sodium nitroprusside [SNP]) were prepared as a 50-fold concentrated stock in dimethylsulfoxide (DMSO). Phycoerythrin-labeled rabbit anti-human platelet P-Selectin (CD62) monoclonal antibody and phycoerythrin-labeled control antibody were purchased from Becton-Dickinson.

Apheresis platelets were obtained from the Gulf Coast Regional Blood Center (Houston, Tex.) following the overnight incubation at 20 to 24° C. on an orbital shaker. Units were then aliquoted 40 mls/bag into CharterMed 150 ml transfer packs (T-3101, Lakewood, N.J.). An aliquot of the fresh, untreated apheresis platelet unit was retained for the determination of in vitro functional activity as described below. The fresh, untreated platelets were assayed for cell number using a Biochem Immunosystems System 9110 CP+ Hematology Analyzer (Allentown, Pa.). The 40 ml aliquots had the following reagents added via injection through a sterile port: a) 800 µl of DMSO yielding a 2% of DMSO final concentration, b) 10 ml of a 30% DMSO solution, prepared with matched plasma, added with shaking over 15 minutes, yielding a 6% final concentration and c) 800 µl of a 50-fold concentrate of TC yielding a 2% DMSO final concentration. The resulting TC-treated apheresis platelets contained the following final concentrations of reagents: amiloride (0.25 mM), adenosine (0.1 mM), and SNP (50 µM). The treated apheresis platelet units were mixed by gentle shaking and directly placed at −80° C. in aluminum cassette. Following storage, the platelet samples were thawed at 37° C. in a water bath and placed on an orbital shaker set at 70 rpm for 15 minutes. Following thaw, a sample was removed from the storage bag and assayed for cell number as described previously. In addition, a sample was fixed for FACS analysis and evaluated for discoid morphology as described previously. In addition, a sample was fixed for FACS analysis and evaluated for discoid morphology as described below. The remaining aliquot was centrifuged at 950×g for 20 minutes at 22° C. to remove the TC storage solution and the DMSO. The resulting platelet pellet was resuspended to the original sample volume with matched plasma and the platelet cell number was determined. The platelet sample was adjusted with matched platelet poor plasma (PPP) to obtain a platelet concentration of $3 \times 10^8$ cell/ml which was incubated at 37° C. for 30 minutes.

Platelet Aggregation Assay: The washed platelet sample was assessed for aggregation, using ristocetin (25 mg/ml) or a combination of ADP (5 µM) and collagen (5 µg/ml) as the agonist, with a Chronology Whole Blood Aggregometer (560 VS). The aggregation was determined as the percent maximum aggregation using PRP as the baseline and PPP as 100%.

Hypotonic Shock Response (HSR): A washed platelet sample, as described above, was used for the determination of HSR. A 0.5 ml sample of the platelet preparation was placed into each of two cuvettes. An addition of 0.25 ml of PBS was made to the first cuvette to determine the increase in light transmission as a result of dilution. The second aliquot was subjected to an addition of 0.25 ml of water and the percent recovery from hypotonic shock was determined over a 15 minutes time frame. All measurements were made using a Chronology Whole Blood Aggregometer (560 VS).

Extent of Shape Change (ESC): Platelets, prepared as described above, were assayed for extent of shape change according to the BEST group protocol. Briefly, a 0.5 ml aliquot of autologous platelet-poor plasma was placed in the aggregometer with stirring and light transmissions was measured using water as a blank. This process was repeated with a 0.5 ml sample of platelet suspension. The platelet sample was then blanked against PPP and a baseline was established. Subsequently, 20 $\mu$l of 0.1M EDTA was added directly to the platelets followed immediately by 20 $\mu$l of 1 mM ADP. The deflection from the baseline was measured at its peak and the percent ESC was determined by the percent of maximal optical density increase, as previously described.

Stirring Shape Change (SSC): Platelets were prepared as described above. The stirring shape change assay was performed as follows: a 0.5 ml aliquot of autologous platelet-poor plasma was placed in the aggregometer with stirring and light transmission was measured using water as a blank. This process was repeated with a 0.5 ml sample of platelet suspension. The platelet sample was then blanked against PPP and a baseline was established. The stirrer was then turned off and the deflection from the baseline was measured at its peak. The percent SSC was determined in the same manner as the ESC value.

FACS Analysis of GMP-140 Expression: An aliquot of the platelet concentrate (0.1 ml) was added to a mixture of 0.5 ml of PBS and 0.5 ml of 4% paraformaldehyde and mixed well. The sample was incubated at 22° C. for 2 hours followed by incubation at 4° C. Prior to labeling, the sample was washed with PBS, containing 0.1% azide and 0.2% BSA. A 50 $\mu$l sample of the fixed platelets was added to 20 $\mu$l of the anti-P-Selectin monoclonal antibody and incubated at room temperature for 1 hour in the absence of light. A corresponding control antibody was used in parallel to establish baseline binding. The sample was washed with the PBS/azide/BSA buffer and finally resuspended in 40 $\mu$l of the same buffer. Immediately prior to FACS analysis, the sample was diluted to 500 $\mu$l with the PBS/azide/BSA buffer followed by analysis using a Coulter EPICS FACS analyzer. The platelet sample was analyzed for both the percentage of cells expressing the epitope and the mean fluorescence unit, indicating the number of sites/cell.

Light Microscopy: Samples were observed for percent discoid using phase-contrast microscopy with a 40× objective on a light microscope (BH-2, Olympus, Lake Success, N.Y.). All samples were observed as unwashed, concentrated aliquots. The 37° C. samples incubated for 30 minutes in a water bath prior to viewing. The percent discoid was determined by counting 100 cells which were scored as discoid or non-discoid.

In this example, the mean values and standard deviations were generated by standard paired t-test methods.

Platelet Morphology—Cell number The recovery of cell number of the test samples, following the cryopreservation process, is displayed in TABLE 6. The numerical recovery of platelets cryopreserved using 6% DMSO was not statistically different from the TC/2% DMSO-treated platelets. In contrast, cryopreservation using 2% DMSO alone yielded a significant reduction in recovery of cell number as compared to the TC-treated samples (p<0.1). The mean cell number value for the fresh platelets was 1790±304 indicating that overall, no significant loss of cells occurred regardless of the cryopreservation technique. In addition, visual observation of the samples following thaw showed a homogeneous suspension of cells under all conditions with no microaggregates present.

Platelet Morphology—Percent discoid The percentage of the cryopreserved platelet population which display a discoid morphology is shown in TABLE 6. In comparison, fresh platelets displayed a normal, discoid morphology with a mean percent of discoid cells of 79.4±8.1. Following thawing, the platelets cryopreserved with 6% DMSO yielded a significant reduction in the number of platelets displaying a discoid morphology. This loss of discoid shape was also reflected in a large number of ghosts in this population (data not shown). The platelets frozen with 2% DMSO alone displayed an even lower percentage of platelets with a discoid morphology and similar to the 6% DMSO sample, contained cells with abnormal morphological characteristics. In contrast, the TC/2% DMSO-treated platelets displayed morphological characteristics similar to fresh cells and retain a percentage of discoid platelets with greater than 80% of the fresh platelets. Furthermore, the yield discoid platelets in the TC-treated sample, following cryopreservation, was significantly higher than the recovery for the 6% DMSO and 2% DMSO cryopreserved cells (p<0.1 and p<0.05, respectively). Following incubation at 37° C., to allow for a recovery phase, the number of platelets displaying a discoid morphology increased in all of the test samples. While this was most prominent in the platelets cryopreserved with 2% DMSO, both the 6% DMSO and the 2% DMSO cryopreservation methods still yielded platelet populations with significantly lower percentage of discoid cells than the TC-treated sample (p<0.05 and p<0.01, respectively). In fact, following the 37° C. recovery phase, the percentage of discoid platelets in the TC-treated samples was 85% of the value of fresh platelets (68.0 versus 79.4).

Platelet Moryhology—P-Selectin expression Both fresh and stored platelets were analyzed for the surface expression of P-Selectin, an activation marker that is expressed on the cell surface following granule release. The values for the cryopreserved platelets are contained in TABLE 6. The mean percentage of fresh platelets expressing P-Selectin was 23.0±9.7. Following thawing, platelets stored with TC/2% DMSO contained a significantly lower percentage of cells expressing P-Selectin than did either the 6% DMSO- or 2% DMSO-treated platelet samples (p<0.05 for both conditions).

Functional Activity—Agonist-induced aggregation TABLE 7 shows aggregation response of the test samples following stimulation with ristocetin and a ADP/collagen combination. The TC/2% DMSO-treated platelets displayed a similar ristocetin-induced aggregation response to that of the 6% DMSO cryopreserved sample. Compared to platelets cryopreserved with 2% DMSO, the TC/2% DMSO-treated platelets displayed significantly higher ristocetin-induced aggregation (p<0.05). The fresh platelet population yielded an aggregation of 67.2±17.5 in response to ristocetin, which was not statistically higher than the aggregation response for the TC/2% DMSO-treated platelets, which displayed a >80% aggregation response as compared to the fresh cells.

TABLE 7 also shows the aggregation response for the test platelets using a combination of ADP and collagen as the aggregation stimulants. Using this agonist combination, the TC-treated platelets' aggregation response did not differ significantly from either the 2% DMSO or the 6% DMSO control platelets. The mean percent aggregation for fresh platelets was 79.4±13.2, indicating that, unlike the effect with ristocetin, all test groups lost 50% of the aggregation potential to the ADP/collagen combination, following cryopreservation.

Functional Activity—Shape change ESC is an optical measurement of the morphological discoid to spherical shape change platelets undergo in response to agonist-induced activation. The data in TABLE 7 demonstrates that the TC-treated platelets yielded significantly higher agonist-induced shape change as compared to the 6% DMSO and the 2% DMSO control samples (p<0.01 and p<0.05, respectively). In fact, the TC-treated platelets displayed almost a 2-fold higher ESC than the platelets cryopreserved by the conventional 6% DMSO method. The mean value for the fresh platelets was 26.4±5.3, indicating a 50% loss of shape change activity for the TC-treated population. Interestingly, this is a similar amount of functional loss as seen with ADP/collagen-induced aggregation. Since ADP serves as the agonist in this technique, the decrease in ESC may reflect a defect in the ADP response as opposed to the direct loss of ESC activity. Stirring shape change is an optical measurement of the discoid platelet population present in a sample. The optical deflection in response to changing stir speeds, observed in SSC, reflects the non-uniform tumbling of a discoid platelet as opposed to the uniform motion of a spherical platelet which causes no deflection. Similar to the results from the microscopic determination of percent discoid, the SSC values for the TC-treated platelets were significantly higher than the 6% DMSO- and 2% DMSO-treated platelets (p<0.05 for both samples). Fresh platelets had a mean SSC value of 21.8±2.2. As opposed to the direct determination of percent discoid, which demonstrated that the TC-treated platelets displayed a discoid population 80% of the fresh value, the SSC determination yielded a TC-treated platelet value which was 63% of fresh cells.

Functional Activity—Hypotonic shock response HSR is a measurement of the ability of platelets to respond to hypotonic stress, thus reflecting the overall viability and metabolism of the platelet population. As shown in TABLE 7 TC-treated platelets were significantly better than both the platelet samples cryopreserved with 6% DMSO or 2% DMSO (p<0.01and p<0.05, respectively). Moreover, similar to the ESC data, the TC-treated platelets displayed almost 2-fold higher HSR than the samples cryopreserved with 6% DMSO by the conventional method. Compared to fresh platelets, which displayed a man HSR value of 92.3±5.7, the TC-treated platelet population yields 50% of the HSR activity. This is similar to the ESC results, which indicate that both assay equally reflect changes associated with cryopreservation.

In view of the above, one of ordinary skill in the art should appreciate that as a consequence of the biochemical stabilization of the platelets, the requirements for cryoprotectant can be diminished. In our preservation system, the amount of DMSO needed for optimal results is reduced 3-fold from the conventional 6% to a 2% final concentration. As a result of this reduction in cryoprotectant, the preparation of platelet units prior to freezing is simplified. The cryopreservation components, TC and DMSO, are added as a single, bolus injection, with no need for the slow addition process. In addition, the bolus addition results in no dilution of the platelet concentration. Moreover, the TC-treated platelet units can be directly placed in a conventional −80° C. freezer, with no need for controlled rate freezing or storage at unconventional temperatures.

Following cryopreservation, the TC-treated platelets display superior retention of many in vitro functional parameters compared to platelets cryopreserved with 6% DMSO by conventional procedures. The quality of stored platelets, though, can be defined by a group of in vitro tests which define the overall quality of the platelet population and which can be correlated to subsequent in vivo survival and function.

The first in vitro trait we examined was the morphology of the stored platelets, which is expressed as the percentage of the cell population that retained the endogenous discoid shape. The population of TC-treated cryopreserved platelets contained a high number of cells which are discoid, equal to 80% of the starting population. Furthermore, the percent discoid of a standard 22° C., 5-day old PC ranges from 50% to 70%, indicating equivalence between the TC-treated cryopreserved sample and a normal transfusable unit. The percentage of cells in a platelet population which displays a discoid morphology is considered a good predictor of circulatory survival.

The second morphological parameter we measured was the storage-induced expression of the activation marker P-Selectin. The expression of P-Selectin has been associated with clearance by the reticuloendothelial system. The TC-treated platelets displayed a significantly reduced expression of this clearance marker as compared to conventionally cryopreserved platelets. Indeed, <50% of platelets stored at 22° C. for 5-days express P-Selectin on their surface, indicating that the TC-treated cryopreserved cells display superior retention of intact granules, which has been correlated with in vivo viability.

With regards to in vitro functional activity, both ESC and HSR are considered pertinent indicators if in vivo circulatory potential. The TC-treated, cryopreserved platelets yield two-fold higher retention of ESC and HSR as compared to cells cryopreserved with 6% DMSO. While the values for the TC-treated platelets were 50% of the fresh platelets' results, the ESC and HSR results were within the range seen for standard 5-day 22° C. stored PC Furthermore, ESC and HSR values show a strong correlation with in vivo survivability Therefore, the TC-treated platelets, which have twice the values of conventionally cryopreserved platelets, could yield twice the in vivo recovery rate, on the order of 60% to 70% recovery of the infused dose.

The final in vitro parameter analyzed was the response to agonist-induced aggregation as a measurement of hemostatic function. Previous in vivo tests have demonstrated that conventionally cryopreserved platelets perform well in terms of hemostasis. Both the TC-treated and the 6% DMSO treated platelets displayed good aggregation in response to ristocetin yielding values which were not statistically different than the value for fresh platelets. In contrast, while both samples yielded similar response to ADP/collagen stimulation, these values were only 50% of fresh cells. Interestingly, 22° C. stored platelets also displayed a significant reduction of in vitro ADP aggregation following storage, but this response is reversed following transfusion.

The overall evaluation of in vitro parameters of PC cryopreserved with TC and 2% DMSO, as compared to the conventional 6% DMSO procedures, demonstrates that the TC-treated cells display statistically superior retention of morphological and in vitro functional characteristics, many of which have been shown to be directly correlated with in vivo recovery and survival.

TABLE 6

| Assays | 6% DMSO mean +/− std dev (range) | 2% DMSO mean +/− std dev (range) | TC with 2% DMSO mean +/− std dev (range) | p value versus 6% DMSO | p value versus 2% DMSO |
|---|---|---|---|---|---|
| Cell Number ($\times 10^3/\mu l$) | 1859 +/− 291 (1563 to 2335) | 1797 +/− 302 (1447 to 2154) | 1876 +/− 273 (1584 to 2215) | N.S.* | p < 0.1 |
| Percent Discoid | 48.8 +/− 7.7 (41 to 58) | 32.0 +/− 11.5 (18 to 45) | 63.8 +/− 17.0 (36 to 81) | p < 0.01 | p < 0.05 |
| Percent Discoid − 37° C. | 54.0 +/− 4.9 (46 to 58) | 50.0 +/− 6.0 (44 to 59) | 68.0 +/− 4.8 (64 to 70) | p < 0.05 | p < 0.01 |
| P-Selectin (% cell expressing) | 49.4 +/− 11.2 (37.8 to 62.7) | 53.6 +/− 6.7 (42.0 to 58.7) | 38.7 +/− 11.9 (25.2 to 52.9) | p < 0.05 | p < 0.05 |

*N.S. = not significant

TABLE 7

| Assays | 6% DMSO mean +/− std dev (range) | 2% DMSO mean +/− std dev (range) | TC with 2% DMSO mean +/− std dev (range) | p value versus 6% DMSO | p value versus 2% DMSO |
|---|---|---|---|---|---|
| Ristocetin Aggregation (%) | 56.4 +/− 18.5 (27 to 73) | 38.0 +/− 25.5 (0 to 68) | 55.2 +/− 12.4 (43 to 73) | N.S.* | p < 0.05 |
| ADP/Collagen Aggregation (%) | 37.8 +/− 17.1 (16 to 61) | 30.8 +/− 11.5 (15 to 43) | 34.0 +/− 7.1 (25 to 45) | N.S. | N.S. |

*N.S. = not significant

TABLE 8

| Assays | 6% DMSO mean +/− std dev (range) | 2% DMSO mean +/− std dev (range) | TC with 2% DMSO mean +/− std dev (range) | p value versus 6% DMSO | p value versus 2% DMSO |
|---|---|---|---|---|---|
| ESC (% increase in OD) | 6.9 +/− 6.2 (0.7 to 17.0) | 9.3 +/− 5.4 (3.1 to 17.5) | 12.8 +/− 6.4 (7.9 to 23.5) | p < 0.01 | p < 0.05 |
| SSC (% increase in OD) | 11.1+/− 4.8 (4.8 to 17.0) | 10.6+/− 3.6 (7.4 to 15.5) | 13.8+/− 4.6 (8.2 to 20.7) | p < 0.05 | p < 0.05 |
| HSR (% recovery) | 23.8 +/− 9.3 (12.2 to 37.4) | 28.5 +/− 9.5 (3.3 to 36.1) | 45.0 +/− 8.3 (35.6 to 54.7) | p < 0.01 | p < 0.05 |

While the compositions and methods of this invention have been described in terms of preferred embodiments, it will be apparent to those of skill in the art that variations may be applied to the process described herein without departing from the concept, spirit and scope of the invention. All such similar substitutes and modifications apparent to those skilled in the art are deemed to be within the spirit, scope and concept of the invention as it is set out in the following claims.

What is claimed is:

1. A human blood platelet composition comprising
human blood platelets;
physiological saline, plasma or plasma substitutes and combinations thereof; and,
three or more platelet lesion inhibitors selected from an effector of the cyclic adenosine monophosphate second messenger system selected from adenosine, iloprost, prostacyclin, prostacyclin, prostaglandin $E_2$, forskolin, chlolera toxin, isoproterenol, 8-bromo cyclic adenosine monophosphate, dibutyl cyclic adenosine monophosphate, theophylline, isobutylmethyl xanthine, thyrotropin, and auranofin;
an inhibitor acting through the sodium channel selected from amiloride, amiloride analogues, bepridil, flecainide, saxitoxin, benzamil and prajnalium;
an inhibitor acting through the guanosine 5' monophosphate pathway selected from sodium nitroprusside, L-arginine, nitrous oxide, SIN-1, SIN-1A, atrial natriuretic factor, vasopressin, oxytocin, and glyceryl trinitrate;
an inhibitor acting through the cyclooxygenase pathway selected from aspirin, dipyridamole, flurbiprofen, ticlopidine, ketoprofen, ibuprofen, indomethacin, sulfinpyrazone, guanabenz, ursolic acid and benzohydroquinone;
an inhibitor acting through the lipoxygenase pathway selected from aspirin, ticlopidine, ursolic acid, unbelliferone, 5,8,11,14 eicosatetraynoic acid and esculetin;
an inhibitor acting through the phospholipase pathway selected from quinacrine and mepacrine;
an inhibitor acting through the calcium cascade selected from protein kinase C effectors, calcium channel blockers, calcium concentration modifiers, calmodulin effectors, calcium ionophores and adenosine triphosphatase stimulators;
an inhibitor of protease or proteinase selected from heparin and aprotinin; and,
a membrane modifier selected from amantadine, heparin, ticlopidine, pentoxifylline and ajoene;

wherein the three or more platelet lesion inhibitors include amiloride, adenosine and sodium nitroprusside; and wherein the three or more platelet lesion inhibitors are present in a concentration so as to permit the in vitro preservation of the blood platelets.

2. The composition of claim 1 further comprising a cryoprotective agent, the cryoprotective agent being selected from dimethyl sulfoxide, maltodextrin, dextran, hydroxylethyl starch, glucose and combinations thereof.

3. The composition of claim 2 wherein the amiloride has a concentration from about 0.1 mM to about 10 mM, the adenosine has a concentration from about 10 $\mu$M to about 1 mM and the sodium nitroprusside has a concentration from about 2.5 $\mu$M to about 250 $\mu$M.

4. The composition of claim 3 wherein the cryoprotective agent is dimethyl sulfoxide in a concentration from about 0.5% to about 10%.

5. The composition of claim 4, wherein the cryoprotective agent is dimethyl sulfoxide in a concentration is about 2%.

6. A human blood platelet composition comprising human blood platelets;

physiological saline, plasma or plasma substitutes and combinations thereof; and three or more platelet lesion inhibitors including amiloride, adenosine and sodium nitroprusside wherein the three or more platelet lesion inhibitors are present in a concentration so as to permit the in vitro preservation of the blood platelets.

7. The composition of claim 6 further comprising a cryoprotective agent, the cryoprotective agent being selected from dimethyl sulfoxide, maltodextrin, dextran, hydroxylethyl starch, glucose and combinations thereof.

8. The composition of claim 7 wherein the amiloride has a concentration from about 0.1 mM to about 10 mM, the adenosine has a concentration from about 10 $\mu$M to about 1 mM and the sodium nitroprusside has a concentration from about 2.5 $\mu$M to about 250 $\mu$M.

9. The composition of claim 8 wherein the cryoprotective agent is dimethyl sulfoxide in a concentration from about 0.5% to about 10%.

10. A human blood platelet composition comprising human blood platelets;

physiological saline, plasma or plasma substitutes and combinations thereof; and three or more platelet lesion inhibitors including amiloride, adenosine and sodium nitroprusside.

11. A human blood platelet composition comprising human blood platelets;

physiological saline, plasma or plasma substitutes and combinations thereof; and platelet lesion inhibitors including an effector of the cyclic adenosine monophosphate second messenger system selected from adenosine, iloprost, prostacyclin, prostaglandin $E_2$, forskolin, cholera toxin, isoproterenol, 8-bromo cyclic adensine monophosphate, dibutyl cyclic adenosine monophosphate, theophylline, isobutylmethyl xanthine, thyrotropin, and auranofin;

an inhibitor acting through the sodium channel selected from amiloride, amiloride analogues, bepridil, flecainide, saxitoxin, benzamil and prajnalium;

an inhibitor acting through the guanosine 5' monophosphate pathway selected from sodium nitroprusside, L-arginine, nitrous oxide, SIN-1, SIN-1A, atrial natriuretic factor, vasopressin, oxytocin, and glyceryl-trinitrate.

12. The human blood platelet composition of claim 11, wherein the platelet lesion inhibitors are amiloride, adenosine and sodium nitroprusside.

13. A human blood platelet composition comprising human blood platelets;

physiological saline, plasma or plasma substitutes and combinations thereof;

platelet lesion inhibitors including an effector of the cyclic adenosine monophosphate second messenger system selected from adenosine, iloprost, prostacyclin, prostaglandin $E_2$, forskolin, cholera toxin, isoproterenol, 8-bromo cyclic adenosine monophosphate, dibutyl cyclic adenosine monophosate, theophylline, isobutylmethyl xanthine, thyrotropin, and auranofin;

an inhibitor acting through the sodium channel selected from amiloride, amiloride analogues, bepridil, flecainide, saxitoxin, benzamil and prajnalium;

an inhibitor acting through the guanosine 5' monophosphate pathway selected from sodium nitroprusside, L-arginine, nitrous oxide, SIN-1, SIN-1A, atrial natriuretic factor, vasopressin, oxytocin, and glyceryl trinitrate;

and optionally one or more of the following an inhibitor acting through the cyclooxygenase pathway selected from aspirin, dipyridamole, flurbiprofen, ticlopidine, ketoprofen, ibuprofen, indomethacin, sulfinpyrazone, guanabenz, ursolic acid and benzohydroquinone;

an inhibitor acting through the lipoxygenase pathway selected from aspirin, ticlopidine, ursolic acid, unbelliferone, 5,8,11,14 eicosatetraynoic acid and esculetin;

an inhibitor acting through the phospholipase pathway selected from quinacrine and mepacrine;

an inhibitor acting through the calcium cascade selected from protein kinase C effectors, calcium channel blockers, calcium concentration modifiers, calmodulin effectors, calcium ionophores and adenosine triphosphatase stimulators;

an inhibitor of protease or proteinase selected from heparin and aprotinin; and, a membrane modifier selected from amantadine, heparin, ticlopidine, pentoxifylline and ajoene;

wherein the three platelet lesion inhibitors are present in a concentration so as to permit the in vitro preservation of the blood platelets, and retain the functional activity of the blood platelets as measured by percent shape change, hypotonic shock response and aggregation.

14. The human blood platelet composition of claim 13, wherein the platelet lesion inhibitors are amiloride, adenosine and sodium nitroprusside.

* * * * *

UNITED STATES PATENT AND TRADEMARK OFFICE
CERTIFICATE OF CORRECTION

PATENT NO.     : 5,919,614

DATED          : July 6, 1999

INVENTOR(S)    : Stephen A. Livesey; Jerome Connor; Laura M. Currie

It is certified that error appears in the above-identified patent and that said Letters Patent is hereby corrected as shown below:

At Col. 16, line 9, please delete "(μmM)" and insert --(1mM)--

Signed and Sealed this

Twenty-first Day of December, 1999

*Attest:*

Q. TODD DICKINSON

*Attesting Officer*     Acting Commissioner of Patents and Trademarks